(12) United States Patent
Malinin (10) Patent No.: US 7,838,040 B2
(45) Date of Patent: Nov. 23, 2010

(54) METHOD FOR REGENERATING CARTILAGE

(76) Inventor: Theodore Malinin, 360 Atlantic Rd., Key Biscayne, FL (US) 33149

( * ) Notice: Subject to any disclaimer, the term of this patent is extended or adjusted under 35 U.S.C. 154(b) by 634 days.

(21) Appl. No.: 11/564,012

(22) Filed: Nov. 28, 2006

(65) Prior Publication Data

US 2007/0098759 A1 May 3, 2007

Related U.S. Application Data

(62) Division of application No. 10/793,939, filed on Mar. 8, 2004, now abandoned.

(51) Int. Cl.
*A61K 35/34* (2006.01)
(52) U.S. Cl. ........................ 424/548; 424/549
(58) Field of Classification Search .................. None
See application file for complete search history.

(56) References Cited

U.S. PATENT DOCUMENTS

| | | | |
|---|---|---|---|
| 4,440,750 | A | 4/1984 | Glowacki et al. |
| 4,472,840 | A | 9/1984 | Jefferies |
| 4,824,939 | A | 4/1989 | Simpson |
| 4,932,973 | A | 6/1990 | Gendler |
| 5,053,049 | A | 10/1991 | Campbell |
| 5,073,373 | A | 12/1991 | O'Leary et al. |
| 5,290,558 | A | 3/1994 | O'Leary et al. |
| 5,306,311 | A | 4/1994 | Stone et al. |
| 5,405,390 | A | 4/1995 | O'Leary et al. |
| 5,507,813 | A | 4/1996 | Dowd et al. |
| 5,510,396 | A | 4/1996 | Prewett et al. |
| 5,964,805 | A | 10/1999 | Stone |
| 5,968,556 | A | 10/1999 | Atala et al. |
| 6,189,537 | B1 | 2/2001 | Wolfinbarger, Jr. |
| 7,067,123 | B2 | 6/2006 | Gomes et al. |
| 7,335,381 | B2 | 2/2008 | Malinin et al. |
| 2003/0143258 | A1 | 7/2003 | Knaack et al. |
| 2004/0219182 | A1 | 11/2004 | Gomes et al. |
| 2004/0230303 | A1 | 11/2004 | Gomes et al. |
| 2008/0279825 | A1 | 11/2008 | Malinin |

FOREIGN PATENT DOCUMENTS

WO WO 2004/096983 A2 11/2004

OTHER PUBLICATIONS

Cook et al., *J. Bone and Joint Surgery*, 85A, supp. 3, 116-123 (2003).
Crites, Brian M., *Curr. Opin. in Orthop.*, 15, 45-48 (2004).
Johnson, Lanny L., *Clinical Orthopaedics and Related Research*, 391S, S306-S317 (2001).
Lindahl et al., *Novartis Found. Symp.* 249, 175-186, discussion 186-189, 234-238, 239-241 (2003).
Poole, A. Robin, *J. Bone and Joint Surgery*, 85A, supp. 2, 40-44 (2003).
Temenoff et al., *Biomaterials*, 21, 431-440 (2000).
The term "about"—Merriam—Webster Online Dictionry, www.m-w.com, p. 1, Access date Sep. 4, 2006.
Vangsness Jr. et al., *Supplement to the Am. J. Orthopedics*, 29-34 (Feb. 2004).
Lindahl, et al., "Cartilage repair with chondrocytes: clinical and cellular aspects," Natl. Library of Med.—Entrez PubMed, Abstract (2003).
Colnot et al., "Mechanisms of Action of Demineralized Bone Matrix in the Repair of Cortical Bone Defects," Clinical Orthopaedics and Related Research, Lippincott Williams & Wilkins, No. 435, pp. 69-78, Jun. 2005.
Jeffrey, D.R., "Imaging hyaline cartilage," The British Journal of Radiology, 76 (2003), 777-787.
Lavernia, CJ, "Bone and tissue allograft use by orthopaedic surgeons," J Arthroplasty, Jun. 2004; 19(4): 430-5.
Malinin, T & Temple HT, Proc. AAOS, 2004; 5:633.
Urist, Marshall R., "A Chemosterilized Antigen-Extracted Autodigested Alloimplant for Bone Banks," Arch Surg, vol. 110, Apr. 1975.

*Primary Examiner*—Sandra Saucier
*Assistant Examiner*—Satyendra K Singh
(74) *Attorney, Agent, or Firm*—Leydig, Voit & Mayer, Ltd.

(57) ABSTRACT

Disclosed is a method for regenerating articular cartilage in an animal comprising administering a therapeutically effective amount of a non-demineralized particulate articular cartilage having a distribution of particle sizes within the range of from about 60 microns to about 500 microns.

13 Claims, 6 Drawing Sheets

METHOD FOR REGENERATING CARTILAGE

CROSS-REFERENCE TO A RELATED APPLICATION

This patent application is a divisional of copending U.S. patent application Ser. No. 10/793,939, filed Mar. 8, 2004, the disclosure of which is incorporated by reference.

FIELD OF THE INVENTION

This invention pertains to particulate cartilage compositions, processes for preparing particulate cartilage compositions and methods for regenerating articular cartilage.

BACKGROUND OF THE INVENTION

Articular cartilage of higher animals, including man, has very limited potential for repair. Following injuries to articular cartilage, the cartilage generally does not repair itself because of its very limited capacity for regeneration. Repair is dependent on the extent and the depth of injury and the surviving chondrocytes and normal articular cartilage matrix. In injuries involving subchondral bone, there is no regeneration of the cartilage, but there is typically enlargement and progression of the lesion with associated pain. The ultimate goal of treatment of these lesions is restoration of the cartilage, but in most cases this is not achieved.

Adult articular cartilage is not vascularized and, as stated above, lacks the capacity to regenerate itself after sustaining damage (Vangness, C. T., Jr. et al., Am. J. Orth. 33, No. 25S: 29, 2004). When cartilage is cut, without involvement of subchondral bone, the defect often will persist for the duration of the individual's life.

Treatment of articular cartilage defects may be either surgical or non-surgical. Several operative procedures are currently used to repair or remove damaged cartilage in order to prevent further destruction of the joint, decrease pain, and restore function. These include arthroscopic debridement and lavage, subchondral bone stimulating procedures, transplantation of chondrocytes or cartilage autografts and allografts and total knee arthroplasty. However, none of these produces regeneration of the native articular cartilage.

Arthroscopic abrasion arthroplasty was developed as an alternative to open debridement procedures. However, it is not a cartilage repair procedure, but rather merely removes frayed cartilage components as a palliative approach that may delay or defer unicondylar or total knee arthroplasty. The latter, replaces articular surfaces with metal or polyethylene (or similar plastic or ceramic) components. This technique is irreversible and precludes any cartilage regeneration (Johnson, L. L., Clin. Orth. 391S: 306-317, 2001).

Drilling of subchondral bone or microfracture of the same has been used to provide blood supply to fibrocartilage covering of subchondral bone. However, this does not result in regeneration of articular hyaline cartilage.

Tissue and cartilage cell transplantation has the potential to produce cartilage repair at the expense of transplanted cells or intact cartilage. To achieve cartilage repair, transplanted cells and tissues must participate in the development of a permanent three-dimensional matrix. In addition, the cells and tissue must incorporate themselves within the host cartilage.

Several tissue transplantation techniques have been used to treat articular cartilage defects including autologous chondrocytes or mesenchymal cells. Autologous chondrocyte transplantation involves removing a portion of normal articular cartilage from a non-weight bearing portion of the joint. The chondrocytes from this cartilage are segregated and placed in tissue culture. The cells proliferate and produce an adequate number of chondrocytes for reimplantation. Subsequently, the original defect is debrided, covered with a periosteal cover (Crites, B. M., Cur. Opinions in Orthopaedics 15:45, 2004). In the studies to date most successful outcomes have been with circumscribed defects of the knee (Lindahl, A., et al., Novartis Found. Sympos. 249:175, 2003). This technique is limited by the size of the defect and by the amount of healthy cartilage that can be harvested from a given patient. It does not induce regeneration of cartilage, but repopulated the defect with new cells from a different site.

Osteochondral grafts depend on the healing of the junctions between the graft and the recipient. A drawback of the technique is the necessity to anatomically match the curvature and size of the graft with the defect in the recipient. The technique does not produce regeneration of the native cartilage, but depends on obliterations of the defect either with autologous or allogeneic osteochondral grafts.

Bone morphogenetic proteins (BMP's) have been implicated in cartilage repair, as have been other growth factors. However, to date, application of various BMP's to chondral defects has failed to produce full-thickness repair and regeneration. At best, partial healing of full-thickness articular cartilage defects have been reported in a dog. Most other studies of articular cartilage regeneration have been performed on rodents, and none of these has produced complete articular cartilage regeneration.

The present invention provides for ameliorating at least some of the disadvantages of the prior art. These and other advantages of the present invention will be apparent from the description as set forth below.

BRIEF SUMMARY OF THE INVENTION

The invention provides particulate cartilage compositions for stimulating chondrogenesis and producing cartilage regeneration comprising non-demineralized particulate articular cartilage having particle sizes distributed in the range of from about 60 microns to about 500 microns. In some preferred embodiments, the non-demineralized particulate articular cartilage has particle sizes distributed in the range of from about 60 microns to about 250 microns. The particulate articular cartilage may comprise allogeneic cartilage, xenogeneic cartilage or mixtures of allogeneic and xenogeneic cartilage.

In accordance with another aspect of the invention, a process for preparing a particulate cartilage composition for stimulating chondrogenesis and producing cartilage regeneration comprises grinding non-demineralized articular cartilage to particle sizes distributed within the range of from about 60 microns to about 500 microns, where the temperature of the non-demineralized articular cartilage during grinding does not exceed about 50° C. In some preferred embodiments, the process includes grinding the non-demineralized articular cartilage to particle sizes distributed within the range of from about 60 microns to about 250 microns, where the temperature of the non-demineralized articular cartilage during grinding does not exceed about 50° C.

In accordance with a further aspect of the invention, a method for regenerating articular cartilage comprises administering to a cartilage defect a therapeutically effective amount of a cartilage composition comprising non-demineralized articular cartilage having particle sizes distributed within the range of from about 60 microns to about 500 microns. The method may also include administering one or more additional cartilage growth promoting factors. In some embodiments, the inventive cartilage composition may be press-fit into a defect without the use of a cover to contain the material.

Embodiments of the present invention provide many significant advantages over the prior art. For example, the present invention provides cartilage compositions with demonstrable chondrogenic activity. Compositions according to the invention repeatedly and reliably induce new cartilage formation in defects in articular cartilage. The cartilage compositions show complete induced regeneration of articular cartilage defects, in a non-human primate model, the model closest to humans. When placed in a cartilage defect, the inventive cartilage compositions produce new cartilage growth congruitous with the articular surface, even in defects involving subchondral bone. Furthermore, new cartilage formation may be initiated rapidly. In some embodiments, new cartilage formation begins within two weeks and complete coverage of the defect may occur by sixteen weeks.

Advantageously, the present invention also avoids the difficult process of extracting growth factors and proteoglycans and/or similar substances from cartilage with various chemical agents. Additionally, the present invention produces effective cartilage compositions without deleteriously altering the growth factors and other substances present in the cartilage.

DETAILED DESCRIPTION OF THE INVENTION

In accordance with the present invention, particulate cartilage compositions for stimulating chondrogenesis and producing cartilage regeneration comprise non-demineralized particulate articular cartilage. Articular cartilage may be obtained from the articular surfaces of joints, such as from distal femurs, proximal tibias, acetabulums, heads of femurs, and/or heads of radiuses. The cartilage may be removed, for example, with a scalpel blade and is preferably removed down to subchondral bone, without removing any bone. The articular cartilage for use in the present invention may include articular hyaline cartilage and/or fibrocartilage and may comprise allogeneic and/or xenogeneic cartilage.

The articular cartilage is preferably non-demineralized. Preferably, the cartilage is not subjected to harsh chemical treatments, which can alter the inherent natural properties of material within the cartilage. For example, the cartilage is preferably not subjected to demineralization treatments such as treatment with hydrochloric acid, ethylene diamine, and/or other demineralization agents. In some embodiments, the non-demineralized articular cartilage may be subjected to microbiological testing or subjected to other testing protocols that do not deleteriously alter the cartilage.

Additionally, the articular cartilage is not subjected to any physical treatments that may demineralize and/or alter the inherent natural properties of the cartilage. For example, the articular cartilage is preferably not subjected to elevated temperatures, e.g., temperatures greater than about 50° C., that may diminish the chondrogenic activity of the cartilage. However, the articular cartilage may be preserved, e.g., freeze-dried, frozen, and/or dried, after being removed from the joint. One preferred method of preserving articular cartilage is freeze-drying.

The composition includes non-demineralized cartilage particles preferably having a distribution of particle sizes. The articular cartilage particles may have sizes distributed within the range of from about 60 microns to about 500 microns, more preferably distributed in the range of from about 60 microns to about 250 microns. Some compositions, according to the present invention, may include cartilage particles having particle sizes of less than about 250 microns, i.e., cartilage powder. Some compositions may include cartilage particles having a distribution of particle sizes in the range of from about 250 microns to about 500 microns, i.e., cartilage granules. In some embodiments, the composition may comprise a combination of cartilage powder and cartilage granules.

Cartilage compositions according to the present invention may be produced by grinding non-demineralized articular cartilage to produce particles having the preferred distribution of particle sizes. The cartilage may be in the form of dry cartilage, freeze-dried cartilage, frozen cartilage, wet cartilage or mixtures thereof. In one preferred embodiment, the cartilage is freeze-dried. For example, pieces of cartilage obtained from the articular surface of one or more joints is washed in several changes of normal saline, blotted dry, and frozen rapidly, e.g., at 10° C./min or faster, in the vapor phase of liquid nitrogen (about −150° C.) or alternatively in the liquid phase of liquid nitrogen (about −196° C.). After being frozen, the cartilage is preferably rapidly placed directly on the shelves of a freeze-drying apparatus maintained at about −40° C. to about −50° C. (the condenser being cooled to from about −70° C. to about −80° C.) A vacuum level of less than about 100 millitorr is preferably maintained in the freeze-drying chamber during the freeze-drying cycle. The freeze-drying cycle may last an average of about 5 days. During the initial 30-45 minutes of the cycle, the cartilage warms from the initial frozen temperature (e.g., about −150° C.) to the temperature of the freeze-drying chamber (e.g., about −40° C.), after which it is maintained at about −40° C. for the remainder of the cycle. Preferably, the moisture content of the cartilage is reduced to from about 4 to about 5%. Overdrying is preferably avoided, as this may result in the irreversible alterations of collagen and proteoglycan structures. At the end of the freeze-drying cycle, the chamber is warmed to room temperature, the vacuum released and the freeze-dried cartilage is removed.

The non-demineralized articular cartilage may be ground using any suitable grinding apparatus. For example, any grinding apparatus capable of grinding dry, hard, brittle material in seconds, such as turbo mills, disc mills, toothed disc mills, jet mills or other similar apparatuses are suitable.

Preferably, grinding is performed under conditions that preclude raising the temperature of the non-demineralized articular cartilage to a level that may diminish the chondrogenic activity of the composition. For example, grinding is preferably performed without raising the temperature of the articular cartilage above about 50° C. In some embodiments, grinding is preferably performed without raising the temperature of the cartilage above about 40° C. The temperature of the articular cartilage may be measured in any suitable manner. For example, thermocouples may be used to monitor the temperature of the cartilage directly, e.g., by measuring the temperature of the cartilage immediately after grinding, or indirectly, e.g., by measuring the temperature of the metal in the grinding mill. Continuous grinding in conventional grinding mills for 3-5 minutes can raise the temperature of the material to 70° C. or above. However, operating a grinding mill intermittently may preclude an undesirable rise in temperature. In one embodiment, freeze-dried pieces of cartilage, 1-4 mm in size, may be ground in a grinding mill operating intermittently for 20-30 second intervals.

After each grinding cycle, the cartilage may be sieved. The cartilage may be sieved through sieves of 100 to 500 microns. Sieving may be used to separate cartilage into cartilage powder (i.e., particle sizes of less than 250 microns) and cartilage granules (i.e., particle sizes of 250 to 500 microns). Grinding may be repeated until the desired distribution of particles sizes is obtained.

The present invention also provides a method for regenerating articular cartilage. Therapeutically effective amounts of cartilage composition comprising non-demineralized articular cartilage having particle sizes distributed within the range of from about 60 microns to about 500 microns may be administered at the site of a cartilage defect. The cartilage composition may be implanted at the articular surface and packed into the defect. Advantageously, in some embodiments, the cartilage composition may be packed into the defect with the use of an overlying cover.

Without wishing to be bound to any theory, it is believed that compositions, according to the invention, including non-demineralized particulate cartilage, release cartilage growth factor(s) or other substances that induce regeneration of articular cartilage. The three-dimensional shape of the particles and multiple surfaces, as well as the inventive particle sizes and distributions, enhance diffusion of the cartilage growth factor(s) or other substances from the particles. Furthermore, the absence of harsh chemical treatments and avoidance of elevated temperatures during processing facilitates the production of particles having high chondrogenic activity.

The following example further illustrates the invention but, of course, should not be construed as in any way limiting its scope.

EXAMPLE

Figure 1A:
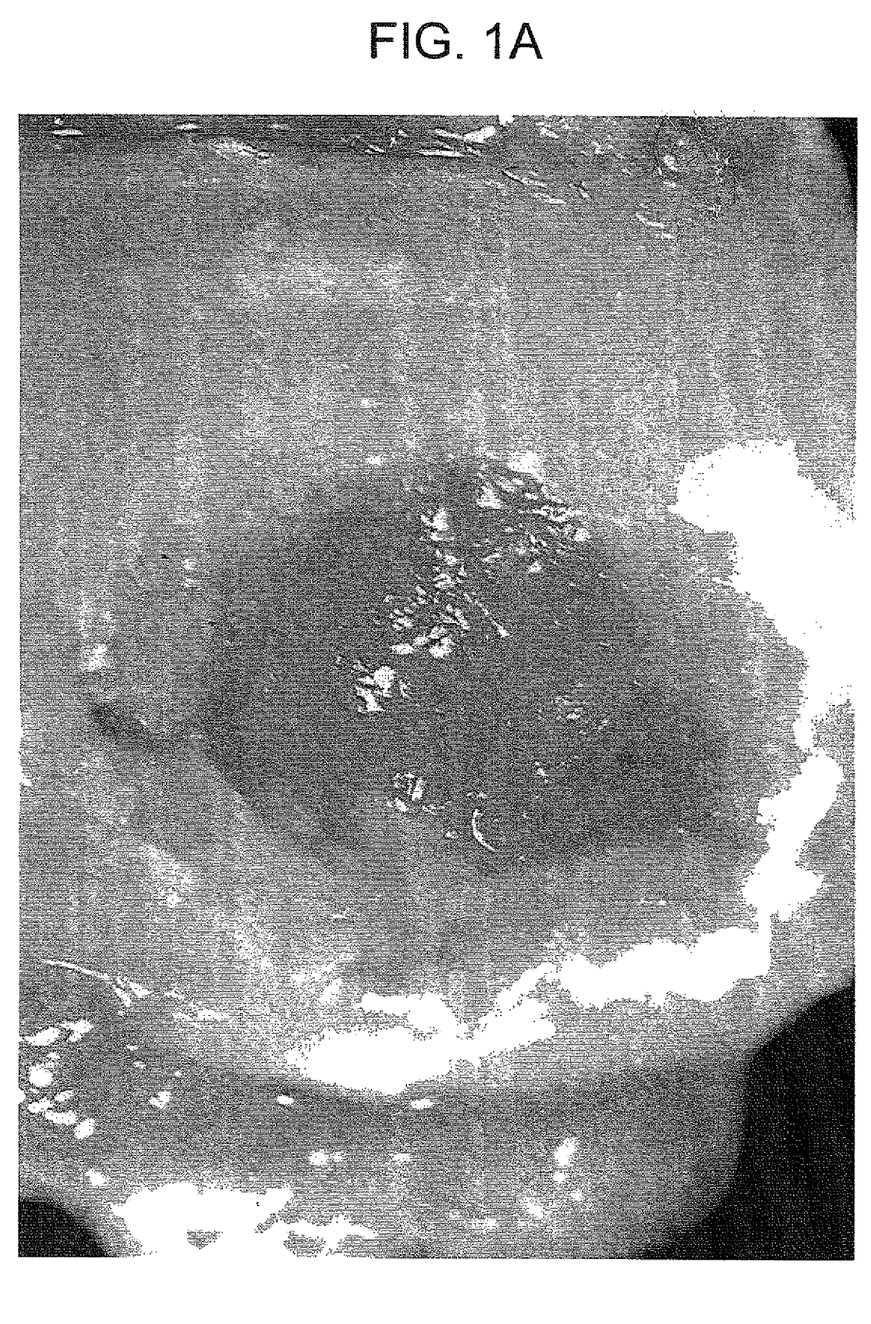
FIGS. 1a-1d show stages of healing of an osteoarticular defect in the medial condyle of the femur of a baboon versus a control defect.
Figure 1B:
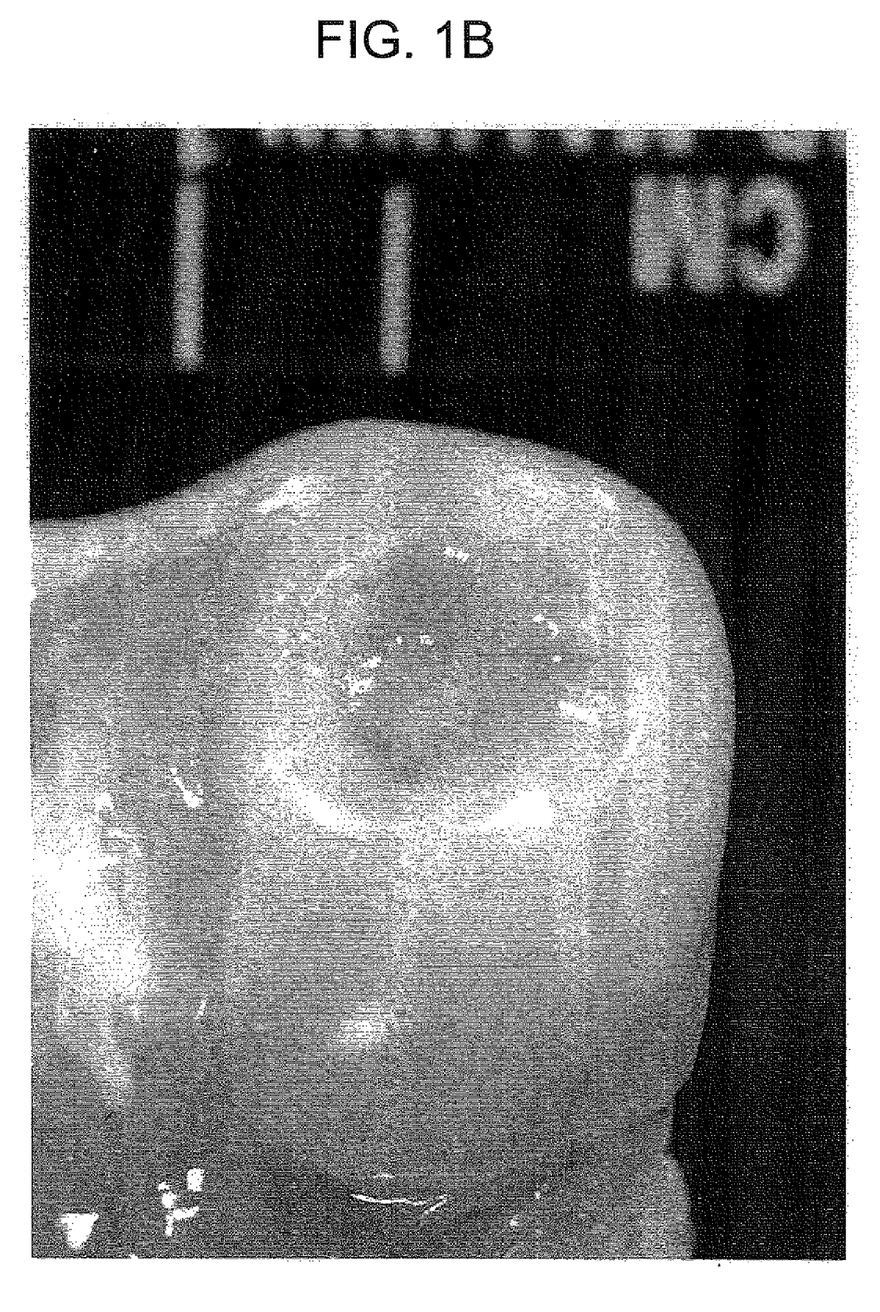
Figure 1C:
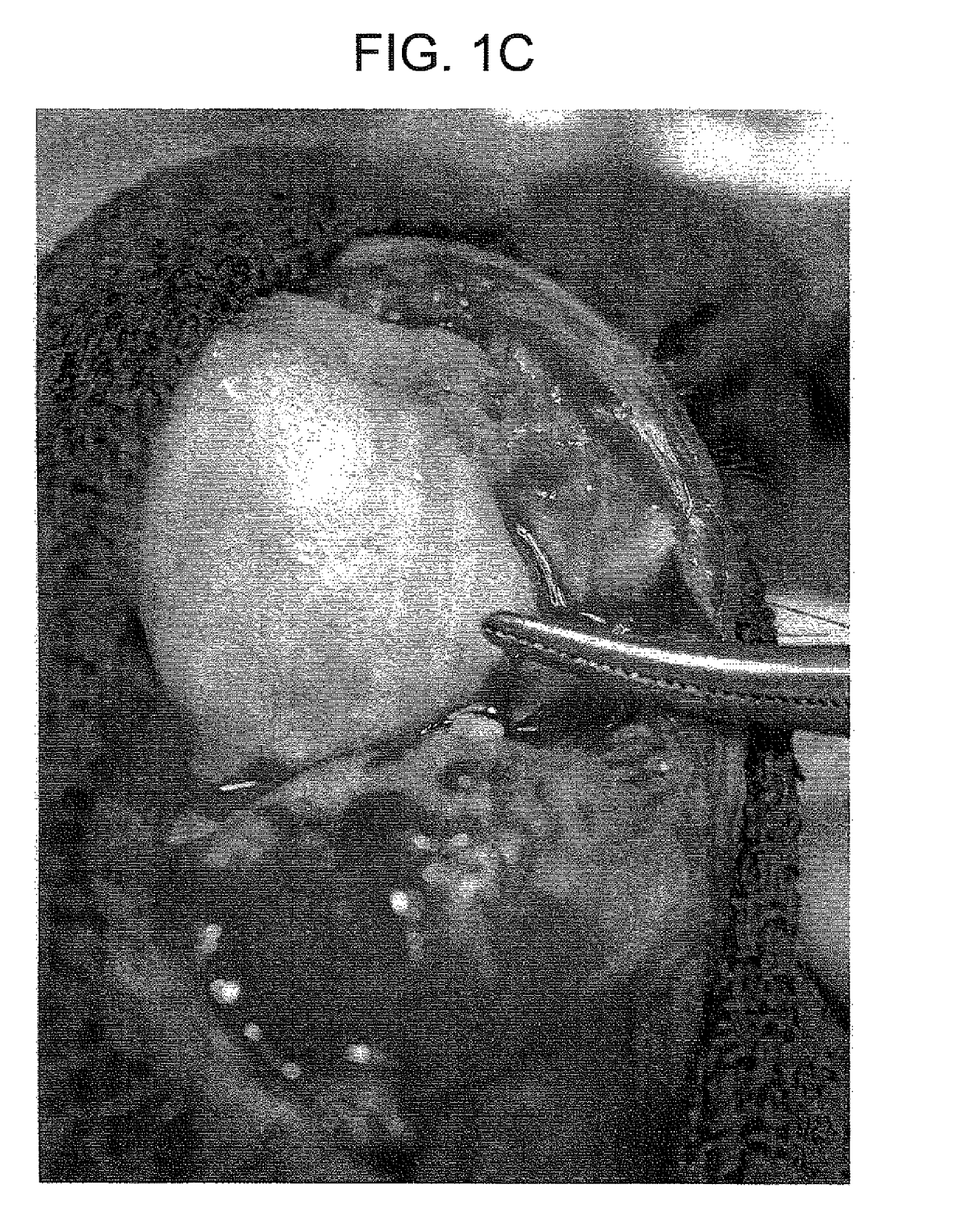
Figure 2A:
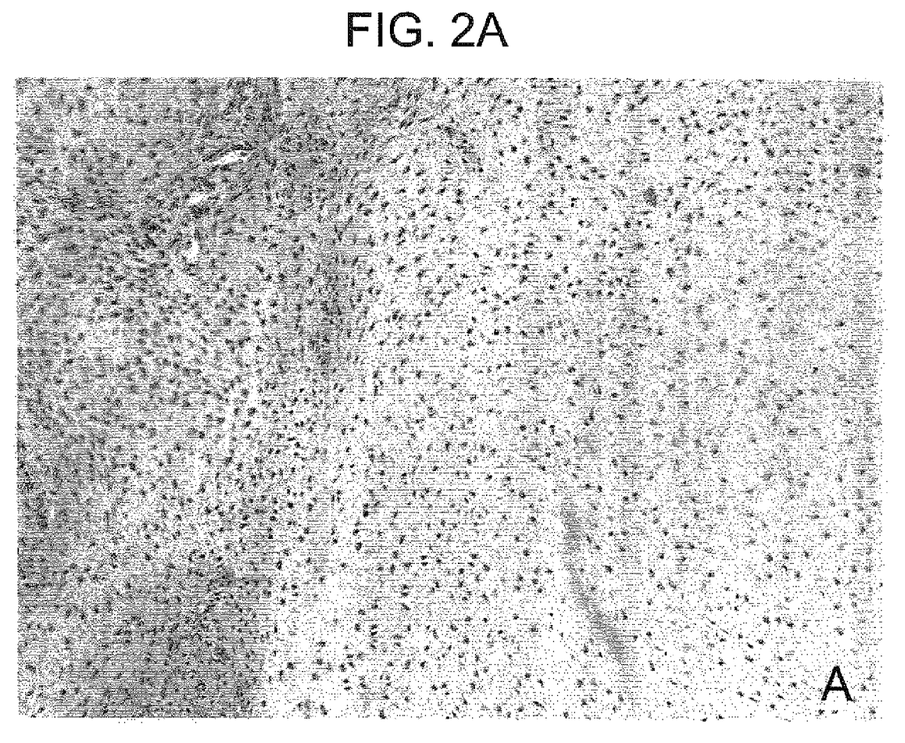
FIGS. 2a-2b show histological preparations of newly formed cartilage.
Figure 2B:
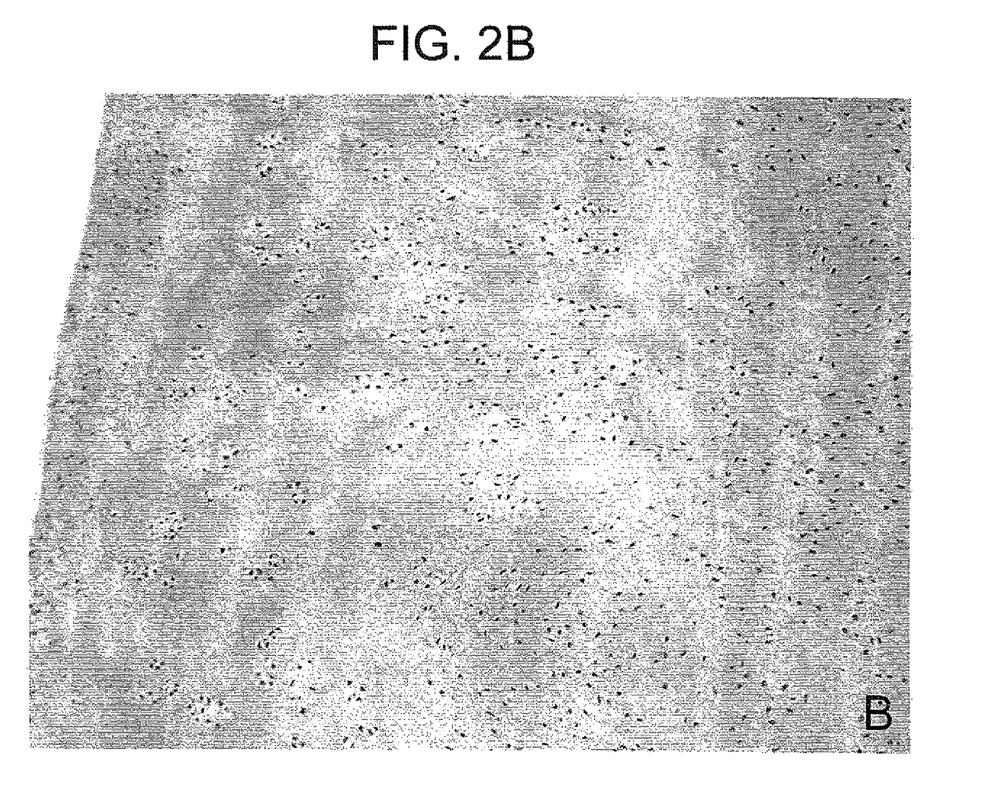

This example demonstrates the chondrogenic activity of the inventive composition in fully immunocompetent non-human primates. Full thickness cartilage defects measuring 10 min×10 mm were created in the medial condyles of the animals. The defects were densely packed with the cartilage composition according to the present invention and were compacted with a tamp. The animals were examined two, six, and sixteen weeks post transplantation and the joints were re-explored. FIGS. 1a-1c are photographs taken at two, six, and sixteen weeks, respectively. Specimens were also taken and were fixed in 10% formalin-Earle's balanced salt solutions. Paraffin sections were cut and stained with homotoxylin and eosin, PAS, Romanowski-Giemsa and Safranin-O stains. FIGS. 2a and 2b illustrate the specimens taken (100×) at six and sixteen weeks, respectively.

Figure 1D:
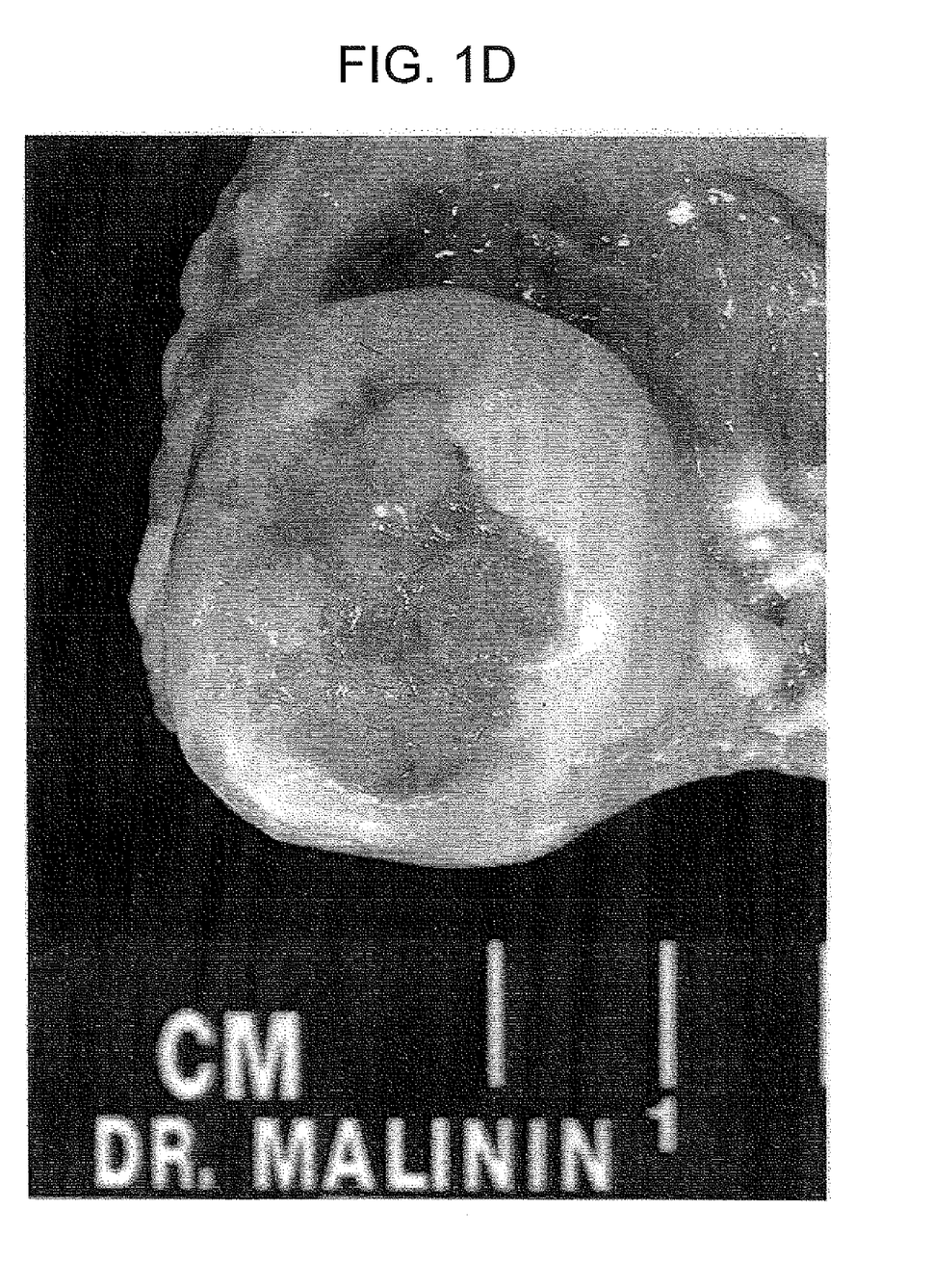

As seen in FIG. 1a, at two weeks post transplantation, granulation tissue is present in the center of the defect and new cartilage is present at the edge of the defect. At six weeks post transplantation (FIG. 1b), new cartilage is formed from the edges of the defect and granulation tissue is no longer present. FIG. 1b also shows the inventive cartilage composition covered with a translucent membrane in the center of the defect. FIG. 2a further illustrates the normal morphology of the hyaline cartilage at six weeks. At sixteen weeks post transplantation, as seen in FIG. 1c, the defect is completely healed and covered with congruous normal appearing cartilage. A section of the newly formed cartilage taken at sixteen weeks is shown in FIG. 2b, and the normal appearing hyaline cartilage can be seen. As a comparison, FIG. 1d illustrates a control, where the defect was left untreated. As seen in the Figure, no evidence of healing is visible and the defect has become larger due to additional fragmentation of the cartilage.

The invention includes the following aspects.

1. An aspect of the invention is a particulate cartilage composition for stimulating chondrogenesis and producing cartilage regeneration comprising non-demineralized particulate articular cartilage having a distribution of particle sizes within the range of from about 60 microns to about 500 microns.

2. In aspect 1 of the invention, the non-demineralized particulate articular cartilage has a distribution of particle sizes within the range of from about 60 microns to about 250 microns.

3. In aspect 1 of the invention, the non-demineralized particulate articular cartilage comprises chemically untreated non-demineralized particulate articular cartilage.

4. In aspect 1 of the invention, the non-demineralized particulate articular cartilage comprises one of hyaline cartilage fibrocartilage, and mixtures thereof.

5. In aspect 1 of the invention, the non-demineralized articular cartilage comprises one of allogeneic cartilage, xenogeneic cartilage, and mixtures thereof.

6. Another aspect of the invention includes a process for preparing a particulate cartilage composition for stimulating chondrogenesis and producing cartilage regeneration comprising grinding non-demineralized articular cartilage to particle sizes distributed within the range of from about 60 microns to about 500 microns, wherein, during grinding, the temperature of the non-demineralized articular cartilage does not exceed about 50° C.

7. In aspect 6 of the invention, during grinding, the temperature of the non-demineralized articular cartilage does not exceed about 40° C.

8. In aspect 6 of the invention, the non-demineralized articular cartilage is not chemically treated.

9. In aspect 6 of the invention, the process comprises grinding one of dry non-demineralized articular cartilage, freeze-dried non-demineralized articular cartilage, frozen non-demineralized articular cartilage, wet non-demineralized articular cartilage, and mixtures thereof.

10. In aspect 6 of the invention, the process comprises grinding one of non-demineralized allogeneic cartilage, non-demineralized xenogeneic cartilage, and mixtures thereof.

11. Another aspect of the invention includes a method for regenerating articular cartilage comprising administering non-demineralized particulate articular cartilage having a distribution of particle sizes within the range of from about 60 microns to about 500 microns.

12. In aspect 11 of the invention, the method comprises administering one or more additional cartilage growth promoting factors to the articular cartilage defect.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Of course, variations of those preferred embodiments will become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the-above-described elements in all possible variations thereof is encompassed by the invention unless otherwise indicated herein or otherwise clearly contradicted by context.

What is claimed is:

1. A method for regenerating articular cartilage in an animal having an articular cartilage defect, the method consisting of administering to the defect a therapeutically effective amount of a cartilage, consisting of non-demineralized particulate articular cartilage having a distribution of particle sizes within the range of from about 60 microns to about 500 microns, wherein the cartilage defect is densely packed and compacted with said cartilage to enhance regeneration of the articular cartilage within the defect.

2. A method for regenerating articular cartilage in an animal having an articular cartilage defect, the method consisting of (a) administering to the defect a therapeutically effective amount of a cartilage, said cartilage consisting of non-demineralized particulate articular cartilage having a distribution of particle sizes within the range of from about 60 microns to about 500 microns and (b) administering one or more additional cartilage growth promoting factors to the articular cartilage defect, wherein the cartilage defect is densely packed and compacted with said cartilage to enhance regeneration of the articular cartilage within the defect.

3. The method of claim 1, wherein the animal is a human.

4. The method of claim 1, wherein the non-demineralized particulate articular cartilage has a distribution of particulate sizes within the range of about 60 microns to about 250 microns.

5. The method of claim 1, wherein the articular cartilage is hyaline cartilage.

6. The method of claim 2, wherein the animal is a human.

7. The method of claim 2, wherein the non-demineralized particulate articular cartilage has a distribution of particulate sizes within the range of about 60 microns to about 250 microns.

8. The method of claim 2, wherein the articular cartilage is hyaline cartilage.

9. A method for regenerating articular cartilage in an animal having an articular cartilage defect, the method comprising administering to the defect a therapeutically effective amount of a cartilage, said cartilage consisting of non-demineralized particulate articular cartilage having a distribution of particle sizes within the range of from about 60 microns to about 500 microns, wherein the cartilage defect is densely packed and compacted with said cartilage to enhance regeneration of the articular cartilage within the defect.

10. The method of claim 9, further comprising administering one or more additional cartilage growth promoting factors to the articular cartilage defect.

11. The method of claim 9, wherein the animal is a human.

12. The method of claim 9, wherein the non-demineralized particulate articular cartilage has a distribution of particulate sizes within the range of about 60 microns to about 250 microns.

13. The method of claim 9, wherein the articular cartilage is hyaline cartilage.

* * * * *